United States Patent [19]
Kropf et al.

[11] Patent Number: 5,941,150
[45] Date of Patent: Aug. 24, 1999

[54] DEVICE FOR DISPENSING AND HOLDING ARTICULATING PAPER

[76] Inventors: Gary Kropf, 7084 Helene Dr., Millington, Tenn. 38053; Cindy Mesler, 15 N. White Station Rd., Memphis, Tenn. 38117

[21] Appl. No.: 08/871,896

[22] Filed: Jun. 9, 1997

[51] Int. Cl.⁶ .................................................. B26D 7/01
[52] U.S. Cl. ................................ 83/231; 83/649; 83/373; 83/277; 83/949
[58] Field of Search .......................... 83/649, 373, 231, 83/232, 277; 225/16; 242/564.3; 226/129

[56] References Cited

U.S. PATENT DOCUMENTS

| | | |
|---|---|---|
| 1,052,344 | 2/1913 | Ipsen . |
| 1,658,989 | 2/1928 | Keck . |
| 3,035,345 | 5/1962 | Barnard .................................. 83/649 X |
| 3,126,631 | 3/1964 | McCarthy et al. ........................... 32/19 |
| 3,138,312 | 6/1964 | Newman .................................. 226/128 |
| 3,470,781 | 10/1969 | Domeny ................................. 83/649 X |
| 3,494,235 | 2/1970 | Postolowski .......................... 83/649 X |
| 3,959,881 | 6/1976 | Kokal, Jr. ..................................... 32/19 |
| 3,971,280 | 7/1976 | Inka ....................................... 83/649 X |
| 4,186,633 | 2/1980 | Baumann et al. ...................... 83/649 X |
| 4,502,621 | 3/1985 | Thatcher .................................... 225/16 |
| 4,712,460 | 12/1987 | Allen et al. ............................. 83/649 X |
| 4,832,229 | 5/1989 | Hackmann et al. ....................... 221/25 |
| 4,856,993 | 8/1989 | Maness et al. ............................. 433/68 |
| 5,181,849 | 1/1993 | Callne ..................................... 433/153 |

Primary Examiner—Rinaldi I. Rada
Assistant Examiner—Ana Luna
Attorney, Agent, or Firm—Walker, McKenzie & Walker, P.C.

[57] ABSTRACT

An apparatus for use with a length of articulating paper. The apparatus includes a container having an interior configured to contain the length of articulating paper; a housing member attached to the container; the housing member having an outlet; conveyor structure for conveying the distal end of the length of articulating paper from the interior of the container to the outlet of the housing member; cutter structure for cutting off a piece of articulating paper from the distal end of the length of articulating paper when the conveyor structure conveys the distal end of the articulating paper to the outlet of the housing member; and holder structure for securely holding the piece of articulating paper after the conveyor structure conveys the distal end of the articulating paper to the outlet of the housing member and after the cutter structure cuts off the piece of the articulating paper from distal end of the length of articulating paper.

4 Claims, 2 Drawing Sheets

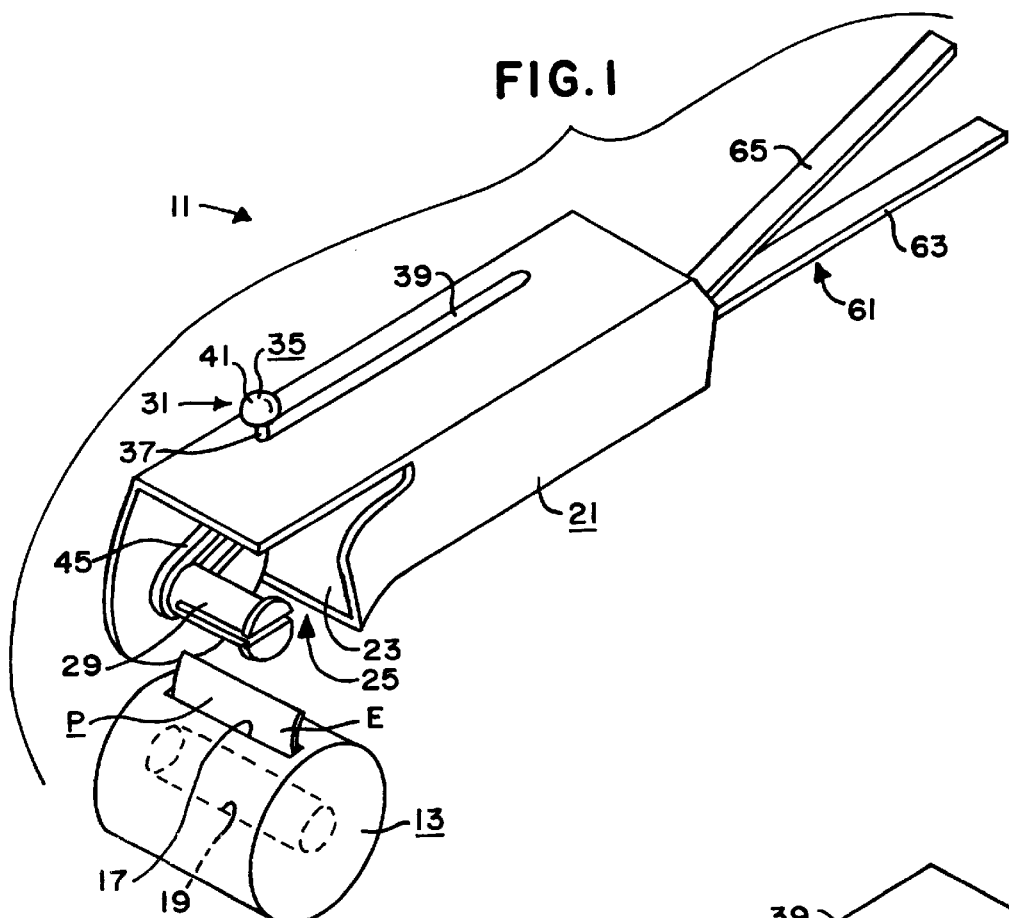
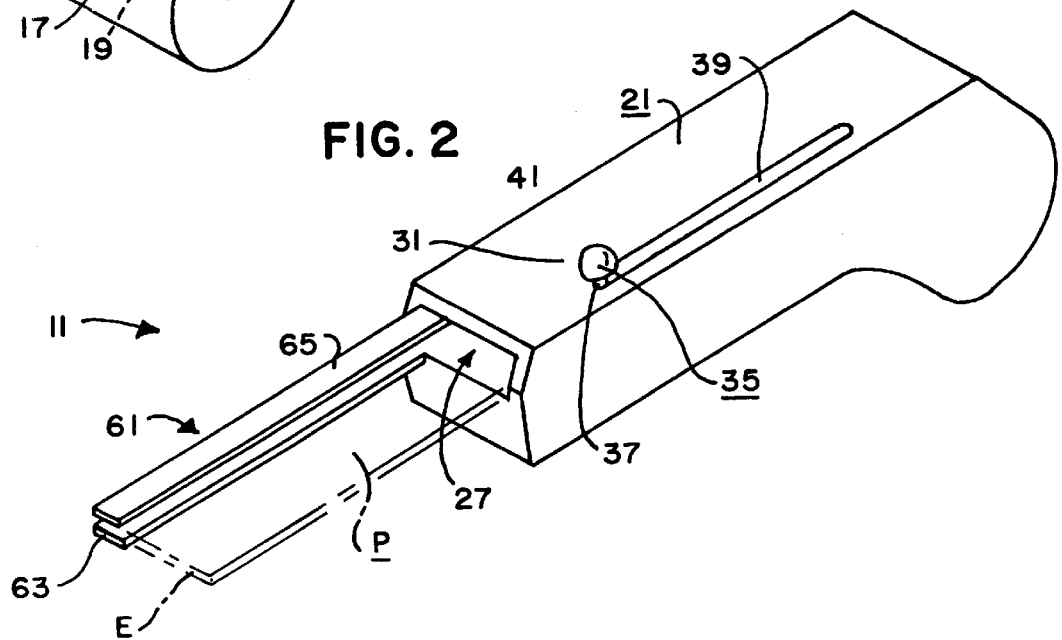

DEVICE FOR DISPENSING AND HOLDING ARTICULATING PAPER

CROSS-REFERENCE TO RELATED APPLICATIONS

Not Applicable.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates to a device for dispensing and holding dental articulating paper.

2. Information Disclosure Statement

A preliminary patentability search conducted in class 433, subclasses 153, 89, 71, 70, 69, and 68; class 221, subclass 36; and class 226, subclasses 129, 128, and 127, produced the following patents which may be relevant to the present invention:

Ipsen, U.S. Pat. No. 1,052,344, issued Feb. 4, 1993, discloses a ticket holder including a housing for holding a plurality of tickets, a thumb operated member mounted within the housing in such a manner that a ticket vendor can dispense a single ticket through a slot in the housing by merely sliding the thumb operated member back and forth. The housing is provided with a spring that forces the tickets against the thumb operated member.

Keck, U.S. Pat. No. 1,658,989, issued Feb. 14, 1928, discloses a device for wetting, cutting and dispensing a length of gummed tape from a roll of gummed tape. The device includes a roller for applying moisture to the tape, a severing mechanism for cutting the tape, and a chain and sprocket mechanism for activating the roller.

McCarthy et al., U.S. Pat. No. 3,126,631, issued Mar. 31, 1964, discloses an articulating paper apparatus for use in the practice of dentistry to test occlusion of natural teeth, etc. The apparatus includes a piece of common disposable articulating paper bent longitudinally to lend stiffness to the paper, and an elongate stick having a slot at one end for receiving the piece of articulating paper and to provide a handle to allow the piece of articulating paper to be easily inserted into a patient's mouth. Dental wax or the like is used to adhere the piece of articulating paper to the stick.

Newman, U.S. Pat. No. 3,138,312, issued Jun. 23, 1964, discloses a device for dispensing note paper of varied selectable lengths from a continuous roll. The device includes a support for a roll of note paper, and a manually operable feed means for selectively feeding a leading segment portion of the roll of note paper to an operable writing position against a backing surface to facilitate the writing of notes, etc., on the leading segment portion of the roll of note paper.

Kokal, U.S. Pat. No. 3,959,881, issued Jun. 1, 1976, discloses a bite intensity detecting articulating paper for marking tooth contact points in differing colors on occlusion. The differing colors correspond to differing biting pressures exerted between the teeth. The paper is impregnated with a plurality of groups of different color ink producing chemicals or individual granules, each of the different groups designed to rupture at different biting pressures for producing resultant various predetermined colors.

Hackmann et al., U.S. Pat. No. 4,832,229, issued May 23, 1989, discloses a dispenser for dispensing strips which contain medicine and can be divided into individual sections as they are dispensed. The dispenser includes a housing having a storage space for strips and a discharge passageway through which strips are dispensed. A ramp interconnects the storage space and passageway, and a feed wheel feeds strips along the ramp. The feed wheel is actuated by an actuating member operable from outside the housing. The actuating member shifts a drive pawl which engages a peripheral gear on the feed wheel.

Maness et al., U.S. Pat. No. 4,856,993, issued Aug. 15, 1989, discloses a contact sensor for detecting points on a grid where the sensor is being contacted on opposing sides by teeth surfaces or other contacting points, especially for measuring dental occlusion. The contact sensor includes two sets of parallel electrodes which are each formed on a thin, flexible supporting sheet, and arranged so that an electrode of one set intersects an electrode of the other set. An electric circuit measures the resistance at the intersection between two opposing electrodes, and provides an output representative of the opposing forces at the intersection. The resistance between each electrode intersection changes as pressure on opposites sides of the intersection changes.

Callne, U.S. Pat. No. 5,181,849, issued Jan. 26, 1993, discloses an articulating paper holder which has an elongated handle and an elongated holding arm. The holding arm is securely attached to and extends from the handle. The holding arm includes a holding means for securely holding a piece of articulating paper for imprinting occlusion contact patterns.

Nothing in the known prior art discloses or suggests the present invention. More specifically, nothing in the known prior art discloses or suggests an apparatus including a container having an interior configured to contain a length of articulating paper; a housing member attached to the container; the housing member having an outlet; conveyor means for conveying the distal end of the length of articulating paper from the interior of the container to the outlet of the housing member; cutter means for cutting off a piece of articulating paper from the distal end of the length of articulating paper when the conveyor means conveys the distal end of the articulating paper to the outlet of the housing member; and holder means for securely holding the piece of articulating paper after the conveyor means conveys the distal end of the articulating paper to the outlet of the housing member and after the cutter means cuts off the piece of the articulating paper from distal end of the length of articulating paper.

BRIEF SUMMARY OF THE INVENTION

The present invention provides an apparatus used to check the dental occlusion of a patient by having the patient bite, either in centric bite or lateral excursion, into a piece of articulating paper, thereby marking contact points, prematurities, etc. Until the present invention, the changing of articulating paper was typically done in a time consuming, manual process of tearing off new paper from a separate dispenser and placing the new paper into an simple holder. A basic concept of the present invention is to provide an apparatus that contains a roll of articulating paper and that allows the dentist to easily change articulating paper by merely advancing a new piece from the length thereof held by the apparatus.

The apparatus of the present invention includes, in general, a container having an interior configured to contain a length of articulating paper; a housing member attached to the container; the housing member having an outlet; conveyor means for conveying the distal end of the length of articulating paper from the interior of the container to the outlet of the housing member; cutter means for cutting off a piece of articulating paper from the distal end of the length of articulating paper when the conveyor means conveys the distal end of the articulating paper to the outlet of the housing member; and holder means for securely holding the piece of articulating paper after the conveyor means conveys the distal end of the articulating paper to the outlet of the housing member and after the cutter means cuts off the piece of the articulating paper from distal end of the length of articulating paper.

One object of the present invention is to provide an apparatus that saves valuable chairtime for the dentist and still maintains an effective infection control barrier between patients, since each piece of articulating paper is sliced or cut within the handle of the apparatus before being exposed to the patient's saliva, etc.

Another object of the present invention is to provide an apparatus in two basic parts: (1) an autoclavable, paper-advancing holder, and (2) an articulating paper cartridge.

BRIEF DESCRIPTION OF THE SEVERAL VIEWS OF THE DRAWINGS

FIG. 1 is a partially exploded perspective view of the apparatus of the present invention as taken generally from the rear right.

FIG. 2 is a perspective view of the apparatus of the present invention as taken generally from the front left, showing a length of articulating paper in broken lines.

DETAILED DESCRIPTION OF THE INVENTION

Figure 3:
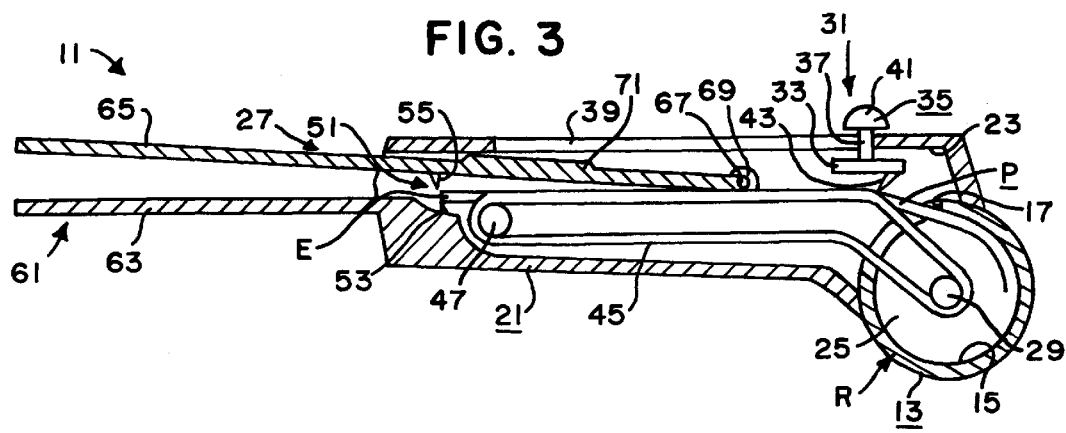
FIG. 3 is a slightly enlarged, somewhat diagrammatic longitudinal sectional view of the apparatus of the present invention, showing the apparatus of the present invention in a fully opened position.

The preferred embodiment of the apparatus 11 of the present invention is especially designed for use with a length of articulating paper P, and is shown in FIGS. 1–6. More specifically, the apparatus 11 is intended to be used by a dentist to dispense and hold a length of articulating paper P to check the dental occlusion of a patient by having the patient bite, either in centric bite or lateral excursion, into the articulating paper P.

The articulating paper P is preferably provided in an elongated roll R having a distal end E, and may be constructed in various manners out of various materials as will now be apparent to those skilled in the art. Standard articulating paper is an off-the-shelf, disposable dental supply consisting, in general, of a sheet of carbon or carbon-like paper with carbon or the like on both sides thereof. A single piece of articulating paper is sized to allow a dentist to easily insert a portion thereof between a patient's teeth to test occlusion of the patient's teeth, etc.

The apparatus 11 includes a container or cartridge 13 having an interior 15 configured to contain the length of articulating paper P. More specifically, the interior 15 of the container 13 is sized to hold the roll R of articulating paper P. The container 13 may consist of a can-like member having a slot or opening 17 in one side for allowing the distal end E of the roll R of articulating paper P to pass therethrough. The container 13 preferably has a rotatable drum or center column 19 about which the roll R of articulating paper P is wound. The column 19 is preferably hollow and communicates through at least one end of the outer housing of the container 13 for reasons which will hereinafter become apparent.

The apparatus 11 includes a housing member 21 attached to the container 13. The housing member 21 provides a holder or handle for the apparatus 11. The housing member 21 may be manufactured in various designs to allow a dentist to easily hold and manipulate the apparatus 11. The housing member 21 has a hollow interior 23 with an inlet 25 and an outlet 27 for allowing the distal end E of the roll R of articulating paper P to pass therethrough. The housing member 21 may include an axle or post for removably receiving the container 13. More specifically, the housing member 21 preferably includes a stub-type axle or post 29 attached to a wall of the housing member 21 adjacent the inlet 25 as clearly shown in FIG. 1 for extending into the column 19 of the container 13 to removably secure the container 13 relative to the housing member 21 with the opening 17 of the container 13 communicating with the inlet 25 of the housing member 21 so that the distal end E of the roll R of articulating paper P can pass from the interior 15 of the container 13, through the opening 17 of the container 13, through the inlet 25 of the housing member 21, and into the interior 23 of the housing member 21. The post 29 may have a split, springable body shaped or otherwise designed to allow the container 13 to be easily snapped on and off, etc. The post 29 is preferably rotatably attached to the housing member 21 in any manner now apparent to those skilled in the art for helping to rotate the roll R of articulating paper P and thereby cause the distal end E of the length of articulating paper P to be conveyed from through the interior of the container 13.

The apparatus 11 includes conveyor means 31 for conveying the distal end E of the length of articulating paper P from the interior 15 of the container 13 to the outlet 27 of the housing member 21. The conveyor means 31 preferably includes a body 33 for movement from a first position as shown in FIG. 3 to a second position as shown in FIG. 5. The conveyor means 31 also preferably includes a handle member 35 attached to the body 33 of the conveyor means 31 for allowing the user of the apparatus 11 to easily manually move the body 33 of the conveyor means 31 between the first and second positions by merely sliding the handle member 35 between the first and second positions as shown diagrammatically in FIGS. 3–5. Thus, the body 33 preferably consist of a block-like member located within the interior 23 of the housing member 21, and the handle member 35 preferably includes a shaft 37 attached to the body 33 and extending through a slot 39 in the housing member 21, and a knob 41 attached to the outer end of the shaft 37 for allowing the dentist or other user of the apparatus 11 to easily slide the body 33 between the first and second positions by merely pushing on the knob 41 as will now be apparent to those skilled in the art. The slot 39 is elongated and preferably extends lengthwise of the housing member 21 a distance sufficient to allow the shaft 37 to be moved fully between the first and second positions as shown in FIGS. 3 and 5.

The conveyor means 31 preferably includes at least one catch member or pin 43 attached to the body 33 of the conveyor means 31 for causing the distal end E of the roll R of articulating paper P to move when the body 33 of the conveyor means 31 is moved from the first position to the second position. The catch member 43 is especially designed so that it will not cause the distal end E of the articulating paper P to move when the body 33 of the conveyor means 31 is moved from the second position to the first position. The catch member 43 may have a sharp distal end or point directed toward the outlet 27 of the housing member 21 for digging into the surface of the articulating paper P when the body 33 of the conveyor means 31 is pushed from the first position shown in FIG. 3 to the second position shown in FIG. 5. The catch member 43 may have a proximal end that is pivotally attached to the body 33 of the conveyer means 31 so that the distal end of the catch member 43 will pivot upward for sliding backwards over the surface of the articulating paper P without moving the articulating paper P when the body 33 of the conveyor means 31 is pushed from the second position shown in FIG. 5 to the first position shown in FIG. 3, as will now be apparent to those skilled in the art.

Figure 4:
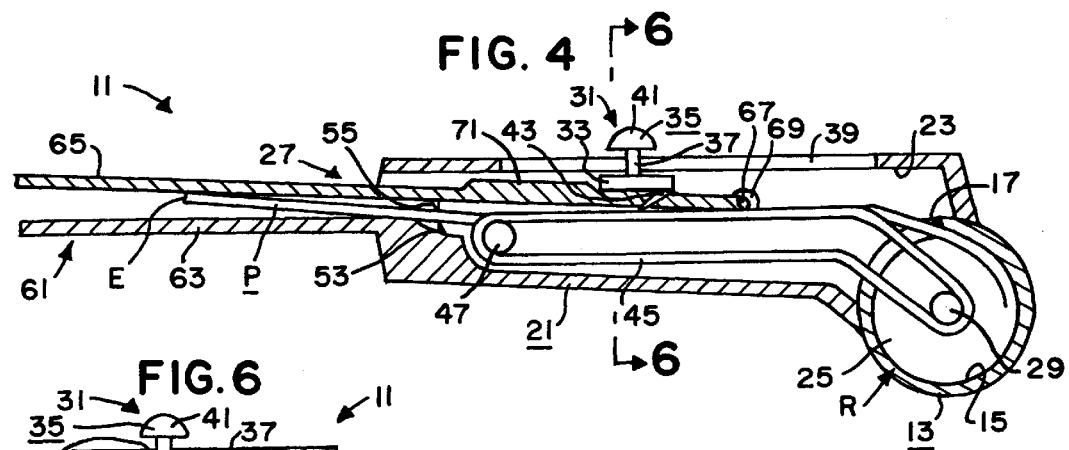
FIG. 4 is an enlarged, somewhat diagrammatic longitudinal sectional view of the apparatus of the present invention similar to FIG. 3 but showing a length of articulating paper partially advanced to an in-use position.
Figure 6:
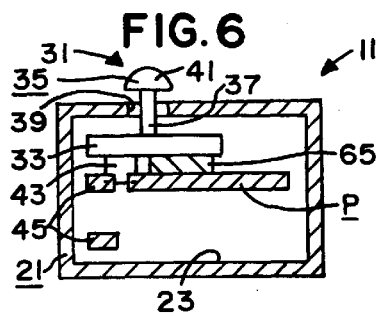
FIG. 6 is a somewhat diagrammatic sectional view substantially as taken on line 6—6 of FIG. 4, on an enlarged scale and with portions omitted for clarity.
Figure 5:
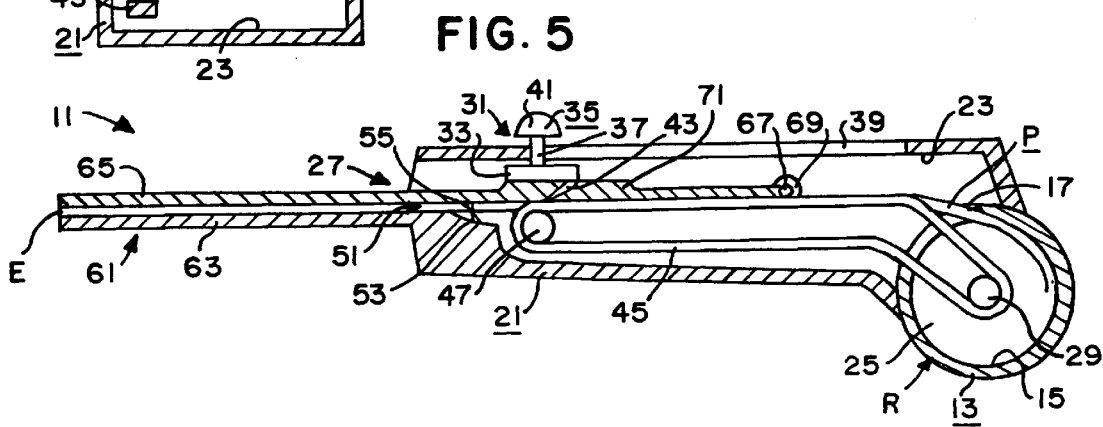
FIG. 5 is an enlarged, somewhat diagrammatic longitudinal sectional view of the apparatus of the present invention similar to FIG. 3 but showing a length of articulating paper fully advanced to an in-use position and showing the apparatus of the present invention in a fully closed position.

The conveyor means 31 may include a pulley cable 45 extending around the post 29 of the housing member 21 and around a guide or axle 47 adjacent the outlet 27 of the housing member 21 as shown in FIGS. 3–5 for coacting with the body 33 and catch member 43 to guide and move the distal end E of the articulating paper P from the interior 15 of the container 13 to the outlet 27 of the housing member 21. More specifically, the pulley cable 45 is preferably designed and positioned so that it will be engaged and moved by the catch pin 43 when the body 33 of the conveyor means 31 is pushed from the first position shown in FIG. 3 to the second position shown in FIG. 5, while allowing the distal end of the catch pin 43 to slide backwards over its surface when the body 33 of the conveyor means 31 is pushed from the second position shown in FIG. 5 to the first position shown in FIG. 3. Movement of the body 33 of the conveyor means 31 from the first position shown in FIG. 3 to the second position shown in FIG. 5 will thus cause the post 29 to rotate which will, thereby, help convey the distal end E of the length of articulating paper P from the interior 15 of the container 13 to the outlet 27 of the housing member 21. The pulley cable 45 preferably has a plurality of transverse grooves on its outer surface for being easily gripped or engaged by the distal end of the catch pin 43 when the body 33 of the conveyor means 31 is moved from the first position shown in FIG. 3 to the second position shown in FIG. 5.

The apparatus 11 includes cutter means 51 for shearing or cutting off a piece of articulating paper P from the distal end E of the length of articulating paper P when the conveyor means 31 conveys the distal end E of the articulating paper P to the outlet 27 of the housing member 21. The cutter means 51 preferably includes a first cutter blade 53 fixedly mounted to the housing member 21 adjacent the outlet 27, and a second cutter blade 55 movably mounted in a position for coacting with the first cutter blade 53 to shear off a portion of the distal end E of the articulating paper P when the conveyor means 31 is moved to the second position as shown in FIG. 5, in a manner which will hereinafter become apparent. Each cutter blade 53, 55 preferably has a knife-like cutting edge with a length equal to or greater than the width of the articulating paper P.

The apparatus 11 includes holder means 61 for securely holding the cut piece of articulating paper P after the conveyor means 31 conveys the distal end E of the articulating paper P to the outlet 27 of the housing member 21 and after or as the cutter means 51 cuts off the piece of the articulating paper P from distal end E of the length of articulating paper P. The holder means 61 preferably includes a first arm member or beak 63 fixedly attached to the housing member 21 and a second arm member or beak 65 moveable between an opened position as shown in FIGS. 1, 3, and 4, spaced from the first arm member 63, and a closed position as shown in FIGS. 2 and 5, in which the second arm member 65 coacts with the first arm member 63 to clamp the cut piece of articulating paper P therebetween. The second arm member 65 is preferably movably attached to the housing member 21 for movement from the opened position shown in FIGS. 1, 3, and 4, to the closed position shown in FIGS. 2 and 5, when the body 33 of the conveyor means 31 is moved from the first position shown in FIGS. 1 and 3, to the second position shown in FIGS. 2 and 5. For example, one end of the second arm member 65 may extend into the interior 23 of the housing member 21, and may be pivotally attached to the housing member 21 by way of a pivot 67 or the like. A spring member 69 may be associated with the second arm member 65 and/or the pivot 67 for normally urging the second arm member 65 to the opened position. A cam member 71 is preferably associated with the second arm member 65 in a manner for being engaged by the body 33 of the conveyor means 31 when the conveyor means 31 is moved from the first position to the second position, causing the second arm member 65 to pivot to the closed position. The cam member 71 may be designed as a raised, integral portion of the second arm member 65 as clearly shown in FIGS. 3–5, with a sloped ramp or the like for allowing the body 33 of the conveyor means 31 to cam the second arm member 65 to the closed position upon engaging and sliding over the cam member 71 as shown diagrammatically in FIGS. 4 and 5. The first and second arm members 63, 65 of the holder means 61 are sized to cover only a portion of the cut piece of articulating paper P when the cut piece of articulating paper P is clamped therebetween so that the cut piece of articulating paper P can be inserted into a patient's mouth for checking the dental occlusion of the patient while held by the holder means 61. More specifically, the width of each arm member 63, 65 is preferably substantially less that the width of the articulating paper P as clearly shown in FIG. 2 so that the cut piece of articulating paper P can be easily positioned between a patient's teeth as the teeth of the patient's upper and lower jaws come together on opposite sides of the cut piece of articulating paper P when the patient's jaws are closed to check the dental occlusion of the patient's teeth, while the cut piece of articulating paper P is securely held between the arm members 63, 65 without interference by the arm members 63, 65, etc., as will now be apparent to those skilled in the art. Because the second cutter element 55 is attached to the second arm member 65 and because the length of the second cutter element 55 is at least equal to the width of the articulating paper P, it will be understood that one end of the second cutter element 55 extends from one side of the second arm member 65 in cantilever fashion. Likewise, the body 33 of the conveyor means 31 is wide enough to cover at least a portion of the second arm member 65 and to position the catch member 43 to one side of the second arm member 65 so that it can extend pass the second arm member to the surface of the articulating paper P, etc.

The various components of the apparatus 11 of the present invention can be manufactured in various manners, out of various materials, and in various specific designs and sizes as will now be apparent to those skilled in the art. Thus, for example, the roll R of articulating paper P is preferably an off-the-shelf item. The container 13 may be molded or otherwise formed out of an autoclavable plastic or the like. A dentist may preload a number of containers 13 with rolls R or articulating paper P and maintain such preloaded containers 13 under sterile conditions or may purchase a number of disposable, preloaded, sterile containers 13, etc. The housing member 21 and first arm member 63 may be molded or otherwise formed as a one-piece, integral unit out of an autoclavable plastic or the like. The body 33, handle member 35, and catch member 43 of the conveyor means 31 may also be molded or otherwise formed out of an autoclavable plastic or the like and mounted in the slot 39 in the housing member 21. The first and second cutter blades 53, 55 may be machined or otherwise formed out of an autoclavable metal and glued or otherwise fixed to the respective housing member 21 and second cutter blade 55 in any manner now apparent to those skilled in the art. The second arm member 65 and pivot 67 may be molded or otherwise formed as a one-piece, integral unit out of an autoclavable plastic or the like, and snapped or otherwise pivotally fixed to the housing member 21 in any manner now apparent to those skilled in the art. The spring member 69 may be an off-the-shelf coil spring or the like positioned between the second arm member 65 and/or pivot 67, and the housing member 21 in such a manner to cause the second arm member 65 to normally pivot to the opened position.

The apparatus 11 of the present invention is used and operation by first snapping a sterile container 13 holding a sterile roll R of articulating paper P onto a sterilized housing member 21 (i.e., by inserting the container 13 over the post 29 of the housing member 21). The distal end E of the articulating paper P is initially advanced to a position adjacent the outlet 27 of the housing member 21 as shown in FIG. 3 by, for example, merely inserting the distal end E through the interior 23 of the housing member 21 along the pulley cable 45 or the like as the container 13 is snapped onto the housing member 21. To then advance the distal end E of the articulating paper P out the outlet 27 and to the holder means 61, the user of the apparatus 11 (e.g., a dentist) can merely push the knob 41 of the conveyor means 31 toward the end of the slot 39 opposite the container 13, using thumb pressure, as illustrated in FIGS. 4 and 5. The catch member 43 will then engage the articulating paper P and/or the pulley cable 45, and urge the distal end E of the articulating paper P through the outlet 27 of the housing member 21. A slight downward pressure on the knob 41 will insure that the catch member 43 securely engages the articulating paper P and/or pulley cable 45. The second arm member 65 will remain in the opened position as the knob 41 is pushed toward the end of the slot 39 opposite the container 13 as clearly shown in FIGS. 3 and 4. However, as the knob 41 approaches the end of the slot 39 opposite the container 13 as shown in FIG. 5, the body 33 of the conveyor means 31 will engage the cam member 71 on the second arm member 65 and force the second arm member 65 to rotate about the pivot 67 toward the closed position. Continued movement of the knob 41 to the end of the slot 39 opposite the container 13 will force the second arm member 65 completely to the closed position, causing the second cutter blade 55 to coacting with the first cutter blade 53 and shear or cut a piece of articulating paper P from the roll R of articulating paper P, and simultaneously cause that cut piece of articulating paper P to be securely held between the first and second arm members 63, 65, as will now be apparent to those skilled in the art.

Although the present invention has been described and illustrated with respect to a preferred embodiment and a preferred use therefor, it is not to be so limited since modifications and changes can be made therein which are within the full intended scope of the invention.

What is claimed is:

1. An apparatus for use with a length of articulating paper having a distal end, the apparatus comprising:

(a) a container having an interior configured to contain the length of articulating paper;

(b) a housing member for attachment to the container; the housing member having an outlet;

(c) conveyor means for conveying the distal end of the length of articulating paper from the interior of the container to the outlet of the housing member; the conveyor means including a body for movement from a first position to a second position, means for causing movement of the body of the conveyor means between the first and second positions, and a pulley cable extending between the interior of the container and the outlet of the housing member;

(d) cutter means for cutting off a piece of articulating paper from the distal end of the length of articulating paper when the conveyor means conveys the distal end of the articulating paper to the outlet of the housing member; and (e) holder means for securely holding the piece of articulating paper after the conveyor means conveys the distal end of the articulating paper to the outlet of the housing member and after the cutter means cuts off the piece of the articulating paper from distal end of the length of articulating paper.

2. An apparatus for use with a length of articulating paper having a distal end, the apparatus comprising:

(a) a container having an interior configured to contain the length of articulating paper;

(b) a housing member for attachment to the container; the housing member having an outlet;

(c) conveyor means for conveying the distal end of the length of articulating paper from the interior of the container to the outlet of the housing member; the conveyor means including a body for movement from a first position to a second position; the conveyor means including a handle member attached to the body of the conveyor means for allowing manual movement of the body of the conveyor means between the first and second positions; the conveyor means including a catch member attached to the body of the conveyor means for causing movement of the length of articulating paper when the body of the conveyor means is moved from the first position to the second position but not when the body of the conveyor means is moved from the second position to the first position; the conveyor means including a pulley cable extending between the interior of the container and the outlet of the housing member;

(d) cutter means for cutting of a piece of articulating paper from the distal end of the length of articulating paper when the conveyor means conveys the distal end of the articulating paper to the outlet of the housing member; the cutter means including a first cutter element fixedly mounted relative to the housing member adjacent the outlet of the housing member, and a second cutter element operatively coupled relative to the conveyor means for movement from a non-cutting position to a cutting position in combination with the first cutter element when the conveyor means conveys the distal end of the roll of articulating paper to the outlet of the housing member; and (e) holder means for securely holding the piece of articulating paper after the conveyor means conveys the distal end of the articulating paper to the outlet of the housing member and after the cutter means cuts off the piece of the articulating paper from distal end of the length of articulating paper; the holder means including a first arm member attached to the housing member and a second arm member moveable between an opened position spaced from the first arm member and a closed position in which the second arm member coacts with the first arm member to clamp the piece of articulating paper therebetween; the second arm member is movably attached to the housing member for movement from an opened position to a closed position when the body of the conveyor means is moved from the first position to the second position; the second cutter element of the cutter means is attached to the second arm member for movement from the non-cutting position to the cutting position when the second arm member is moved from the opened position to the closed position.

3. The apparatus of claim 2 in which the first and second arm members of the holder means are sized to cover only a portion of the piece of articulating paper when the piece of articulating paper is clamped therebetween so that the piece of articulating paper can be inserted into a patient's mouth for checking the dental occlusion of the patient while held by the holder means.

4. The apparatus of claim 2 in which is included a spring member for normally urging the second arm member to the opened position.

* * * * *